United States Patent [19]

Van Nieuw Amerongen et al.

[11] Patent Number: 5,886,054
[45] Date of Patent: Mar. 23, 1999

[54] THERAPEUTIC METHOD FOR ENHANCING SALIVA

[75] Inventors: Arie Van Nieuw Amerongen, Breukelen; Engelmundus Cornelis Ignatius Veerman, Volendam; Willy Alexander Van Der Reijden, Amsterdam-Zuidoost, all of Netherlands

[73] Assignee: Stichting Voor De Technische Wetenschappen, Netherlands

[21] Appl. No.: 687,358

[22] PCT Filed: Feb. 2, 1995

[86] PCT No.: PCT/NL95/00046

§ 371 Date: Sep. 23, 1996

§ 102(e) Date: Sep. 23, 1996

[87] PCT Pub. No.: WO95/20971

PCT Pub. Date: Aug. 10, 1995

[30] Foreign Application Priority Data

Feb. 2, 1994 [NL] Netherlands ............... 9400160

[51] Int. Cl.$^6$ ..................................... A61K 47/00
[52] U.S. Cl. ............... 514/782; 514/772.4; 514/772.6; 514/773; 514/777; 514/781; 514/915
[58] Field of Search ................................ 514/782, 781, 514/773, 777, 772.4, 772.6, 915

[56] References Cited

U.S. PATENT DOCUMENTS

| 4,039,662 | 8/1977 | Hecht et al. | 424/180 |
| 5,078,129 | 1/1992 | Kleinberg et al. | 128/200.14 |

OTHER PUBLICATIONS

The Merck Index (11$^{th}$ Ed.) Budavari et al., Merck and Co., Inc., Rahway, NJ. (1989), p. 959.

*Primary Examiner*—Marianne M. Cintin
*Assistant Examiner*—M. Moezie
*Attorney, Agent, or Firm*—Webb Ziesenheim Bruening Logsdon Orkin & Hanson, P.C.

[57] ABSTRACT

The present invention relates to a therapeutic composition comprising an aqueous solution of at least one polymer and at least one electrolyte, wherein the aqueous solution is preferably buffered and optionally contains at least one mucin. The polymer can be chosen for instance from the group which consists of scleroglucan, guar gum, xanthane gum, sodium carboxymethyl cellulose, hydroxyethyl cellulose, polyacrylic acid and polyvinyl alcohol. The therapeutic composition according to the invention can serve as saliva substitution agent, artificial tear water, in a mouth rinse or in a toothpaste.

2 Claims, 5 Drawing Sheets

THERAPEUTIC METHOD FOR ENHANCING SALIVA

This application is a 371 PCT/NL95/00046 filed Feb. 2, 1995.

The present invention relates to a therapeutic composition for replacing and/or supplementing body fluids such as saliva and tears.

Saliva, tears and the like are of importance for maintaining a healthy environment in the mouth and eyes. It is not however self-evident that an individual can produce sufficient tear water or saliva. People who have had radiation treatment of the oral cavity, cervix or throat are for instance often no longer capable of producing sufficient saliva, because their salivary glands have been entirely or partially destroyed by the radiation treatment.

Another example is formed by those suffering from Sjögren syndrome, who may display symptoms like dry mouth and dry eyes in addition to rheumatic disorders. Sjögren syndrome is a progressive process which has a gradual adverse effect on the saliva production. 60% of the patients consists of women after the menopause. Sjögren syndrome is suspected of being an autoimmune disease.

Dry mouth also occurs regularly in users of medicine, particularly users of sedatives, β-blockers, antihypertension medication, tranquilizers and others medicines which have the side-effect of dulling the nervous system.

A shortage of saliva or tear water can, in addition to the accompanying discomfort and irritation, moreover result in inflammations of the mouth and eyes.

In order to relieve the complaints of dry mouth and eyes saliva substitutes based on carboxymethyl cellulose (CMC) or animal mucins have been proposed (Levine et al., J. Dent. Res. 66:693–698 (1987)). In addition a saliva substitute based on linseed-extract is described in EP-0.511.181. In practice however these known substitutes are not found to be satisfactory. The effective duration of these products is only limited and compared to human saliva they do not possess the desired properties, such as elasticity, viscosity etc.

The object of the present invention is to provide a saliva substitute which approximates the properties of human saliva better than the known products, eliminates the dry sensation in mouth and eyes and needs to be applied less often.

To this end the invention provides a therapeutic composition, comprising a buffered, aqueous solution of at least one polymer and at least one electrolyte.

The polymer is preferably chosen from the group which consists of scleroglucan (in a concentration of about 0.001% to 2% (w/v)), guar gum (about 0.001% to 5% (w/v)), xanthane gum (about 0.001% to 2% (w/v)), sodium carboxymethyl cellulose (for instance of the type Blanose® 7HF, in a concentration of 0.01 to 5% (w/v)), hydroxyethyl cellulose (for instance of the type Natrosol 250 HX Pharm, in a concentration of 0.01 to 5% (w/v)), polyacrylic acid (for instance of the types Carbopol 934P® and Carbopol 974P®, in a concentration of 0.01 to 5% (w/v)) and polyvinyl alcohol (for instance with a degree of hydrolysis between 71.6 and 100 mol %, an ester value between 0 and 285 g KOH/g, a molecular weight between 14,000 and 205,000 and a degree of polymerization between 360 and 4500). Another suitable product can however be chosen as desired from the large supply of available polymers, and particularly polysaccharides.

At least one mucin can optionally be added to the composition. The electrolyte can for instance be chosen from the group consisting of sodium, potassium, fluoride, chloride, phosphate, CNS, rhodanide. The composition can further also contain calcium and/or at least one phosphate compound, as well as flavourings and/or aromatic substances and/or colourings and preservative.

The invention further relates to saliva substitutes or additives, artificial tear water or tear additives, mouth rinses and toothpastes, comprising the therapeutic composition according to the invention.

The advantages of the present invention will become apparent from the example hereinbelow, which is however only intended as illustration and further implies no limitation whatever to the scope of the invention.

EXAMPLE 1

1. Materials

Xanthane gum (95465) originated from Fluka. Alginic acid with a high viscosity (9005-38-3/A-7128) was supplied by Sigma. Carboxymethyl cellulose (Blanose® 7HF) and hydroxyethyl cellulose (Natrosol 250 HX-Pharm) were donations from Aqualon, Rijswijk, the Netherlands. Scleroglucan (Actigum CS11) and Guar gum (Viscogum HV 3 000A) came from Satia, Paris, France. A second type of guar gum (#21255) came from Polysciences Inc., Warrington Pa., USA. All other chemicals came from Merck and were of analytical quality.

2. Sample preparation

All polysaccharides were used directly and dissolved in HPLC-water (J.T. Baker Company, Philipsburg, USA) in the desired concentration. Polysaccharide solutions were obtained by adding the dry polymer base to water while stirring vigorously. After dispersion the solutions were placed on a shaking table for 18 hours to obtain a homogeneous solution.

For the pH-dependency experiments the pH was varied between 3 and 9 by adding NaOH or Hcl. To keep the ionic strength uniform, NaCl was added to the highest added NAOH or Hcl concentration.

The effect of the ionic strength on the rheological properties of polysaccharides was studied by varying the ionic strength between 0 and 500 Mm NaCl.

All polysaccharides were tested for their rheological behaviour after calcium or fluoride treatment and for. their biocompatibility with complete human saliva. The influence of calcium ions and fluoride ions was studied by adding respectively $CaCl_2$ (0–0.5M), NaF (0.6 Mm) to the chosen polysaccharide solutions (Worthington et al., in press (1993)).

After addition of NaOH, Hcl or $CaCl_2$ the solution was incubated at room temperature for three hours.

Determination of the rheological synergistic effects was carried out by mixing equal volumes of polysaccharide solution and non-stimulated complete saliva. Mixtures of water and polymer, and water and saliva served as control. To prevent bacterial and fungal growth in the test samples, the polysaccharide solutions were freshly prepared for each experiment.

Complete human saliva (CHS) was collected by spitting out without any kind of stimulation. It was clarified by centrifugation in a MSE Micro-centaur centrifuge (MSE Scientific Instruments, Sussex, United Kingdom) at 11,600 g at room temperature for 5 minutes and was used immediately for Theological measurements. Clarified complete human saliva is denoted as CCHS.

3. Rheological measurements

In this study an oscillating capillary rheometer was used to determine the viscous part $\eta'$ and the elastic part $\eta''$ of the complex viscosity $\eta^*$ as already described (Van der Reijden et al., Biorheol. 30:141–152 (1993)).

The rheometer was a Vilastic 3 visco-elasticity analyser from Vilastic Scientific Inc., Austin, USA. Comparisons of viscosity and elasticity as in table 2 are made at a shear rate of 1.5 sec$^{-1}$. All measurements were performed at a frequency of 0.5 Hz and at a shear rate between 1 and 1000 s$^{-1}$ and at room temperature (23.0° C.±1.5° C.).

4. Results

Figure 1:
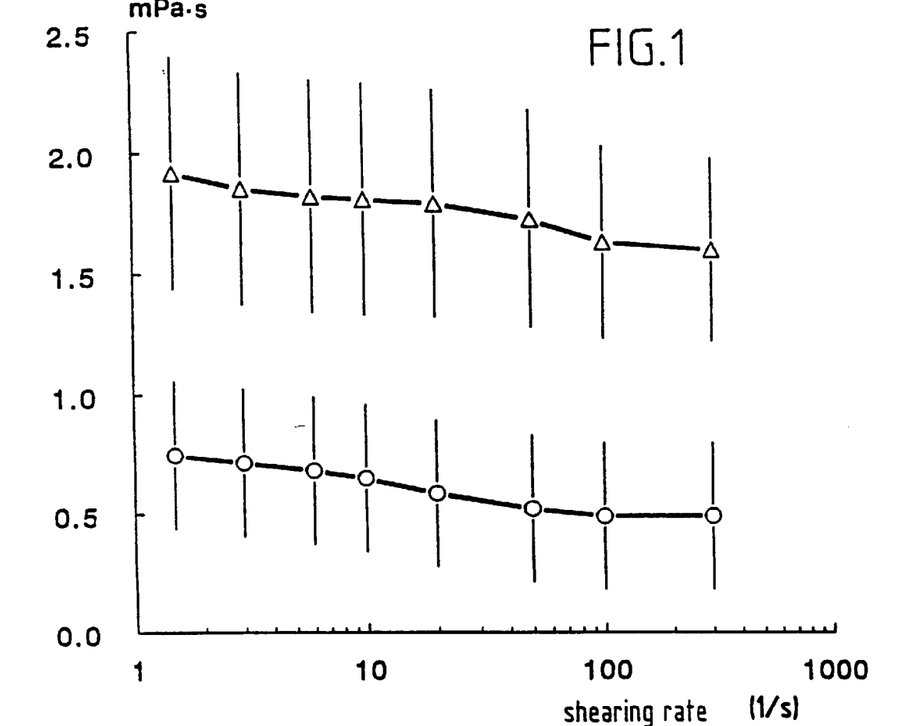
FIG. 1 shows the average viscosity and elasticity as a function of the oscillating shear rate of clarified ron-stimulated complete saliva o: seven healthy people (taken three times). T=13.0° C.±1.5° C.
—Δ— represents the viscosity, and
—o— represents the elasticity. Error lines represent the standard deviation.

The saliva of 7 people was used as reference. A sample was taken from each person three times. The average values of the visco-elasticity measurements of the clarified complete human saliva are shown in FIG. 1.

Figure 2:
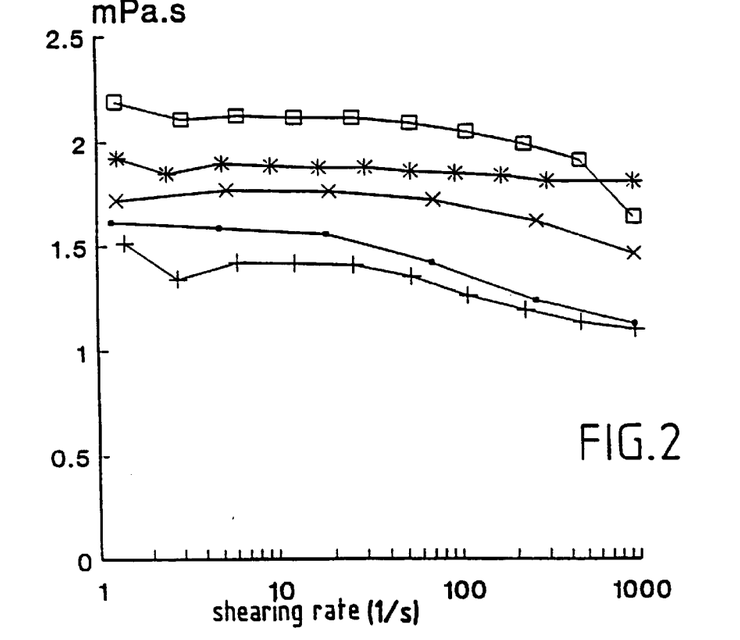
FIG. 2 shows the viscosity of xanthane gum, two types of guar gum and CMC measured as a function of the shear rate. The concentration of the polysaccharides was chosen within the range of the CCHS viscosity.
—■— represents 0.01% xanthane gum;
—+— represents 0.01% scleroglucan;
—*— represents 0.1% guar gum S;
—☐— represents 0.1% guar gum P; and
—×— represents 0.03% CMC.
Figure 3:
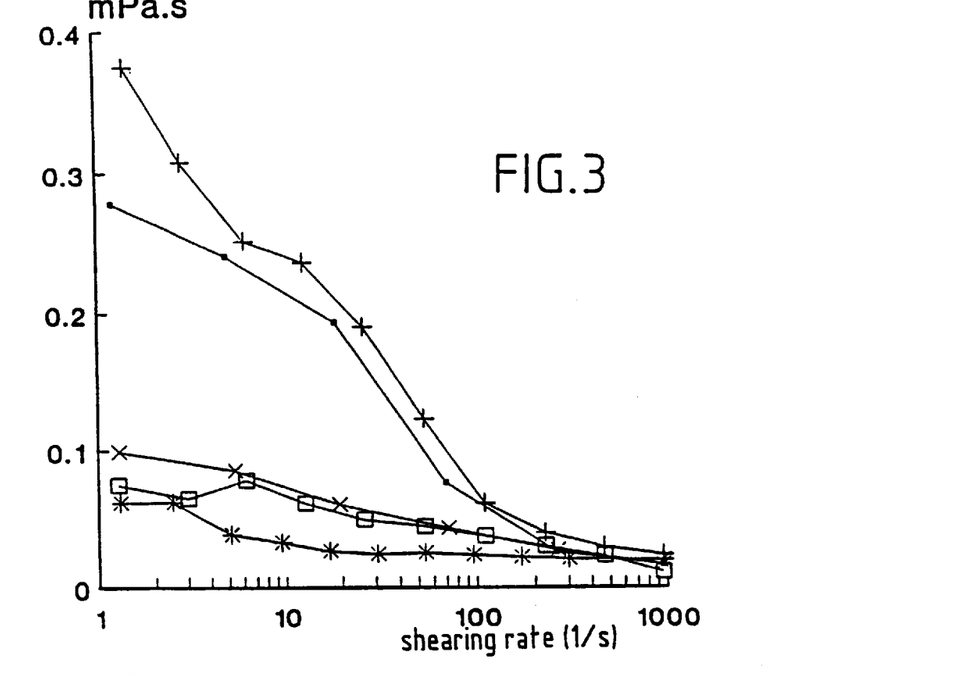
FIG. 3 shows the elasticity of xanthane gum, two types of guar gum and CMC at a concentration in which the viscosity corresponds with the CCHS viscosity.
—■— represents 0.01% xanthane gum;
—+— represents 0.01% scleroglucan;
—*— represents 0.1% guar gum S;
—☐— represents 0.1% guar gum P; and
—×— represents 0.03% CMC.

Inter-individual differences were observed in viscosity as well as elasticity, which are shown by error bars representing twice the standard deviation. The data was obtained from an earlier study (Van der Reijden et al., 1993). It is noteworthy that the viscosity of complete human saliva is only a little pseudoplastic and about 2.07±0.48 mPa·s. The elasticity of complete human saliva is reasonably high compared to its viscosity: 0.77±0.31 Mpa·s. The shear rate dependency of the viscosity of the various polysaccharides tested is shown in FIG. 2, and that of the elasticity in FIG. 3. The shear rate dependency is apparent for all polysaccharides at a concentration of 0.1%. At a concentration which resulted in a viscosity level corresponding with natural saliva, 'pseudoplasticity' was observed for the viscosity and elasticity of xanthane gum and scleroglucan, but hardly so for the other polysaccharides (FIGS. 2 and 3).

Figure 4:
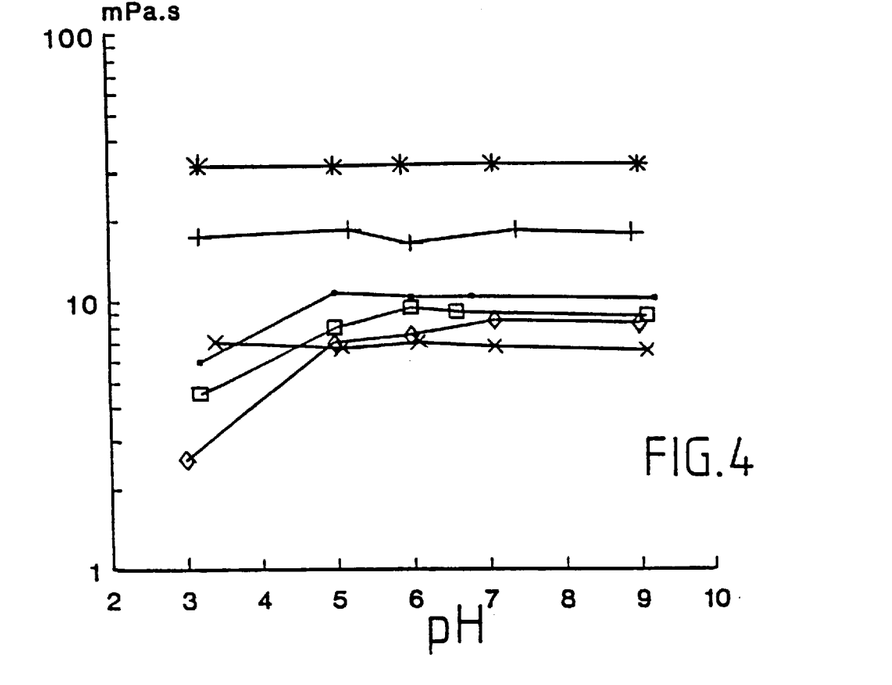
FIGS. 4 & 5 show respectively the pH-dependency of the viscosity and elasticity of polysaccharides, wherein the pH is varied from pH 3 to 9.
—■— represents 0.05% xanthane gum;
—+— represents 0.1% scleroglucan;
—*— represents 0.25% guar gum P;
—☐— represents 0.1% CMC;
—×— represents 0.2% HEC; and
—◊— represents 0.25% alginic acid.
Figure 5:
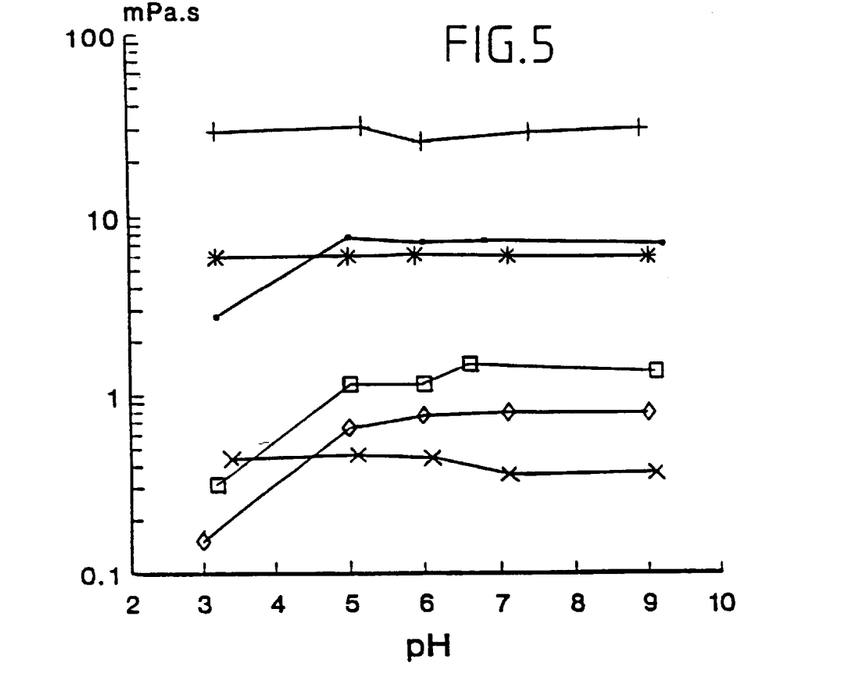
Figure 6:
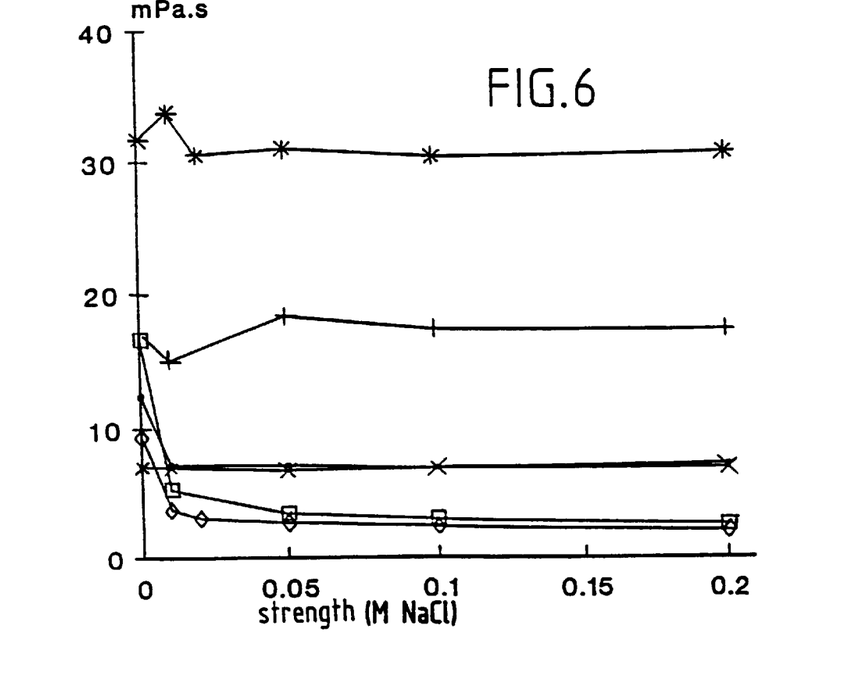
FIGS. 6 & 7 show the ionic strength dependency of respectively the viscosity and elasticity of polysaccharides wherein the NaCl-concentration is varied from 0 to 0.5M NaCl.
—■— represents 0.05% xanthane gum;
—+— represents 0.1% scleroglucan;
—*— represents 0.25% guar gum P;
—☐— represents 0.1% CMC;
—×— represents 0.2% HEC; and
—◊— represents 0.25% alginic acid.
Figure 7:
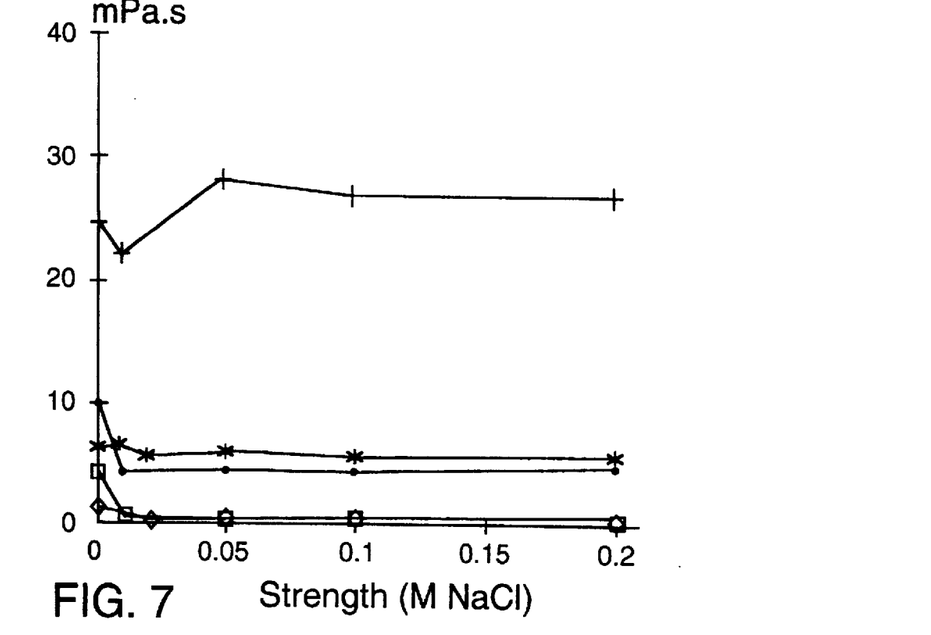
Figure 8:
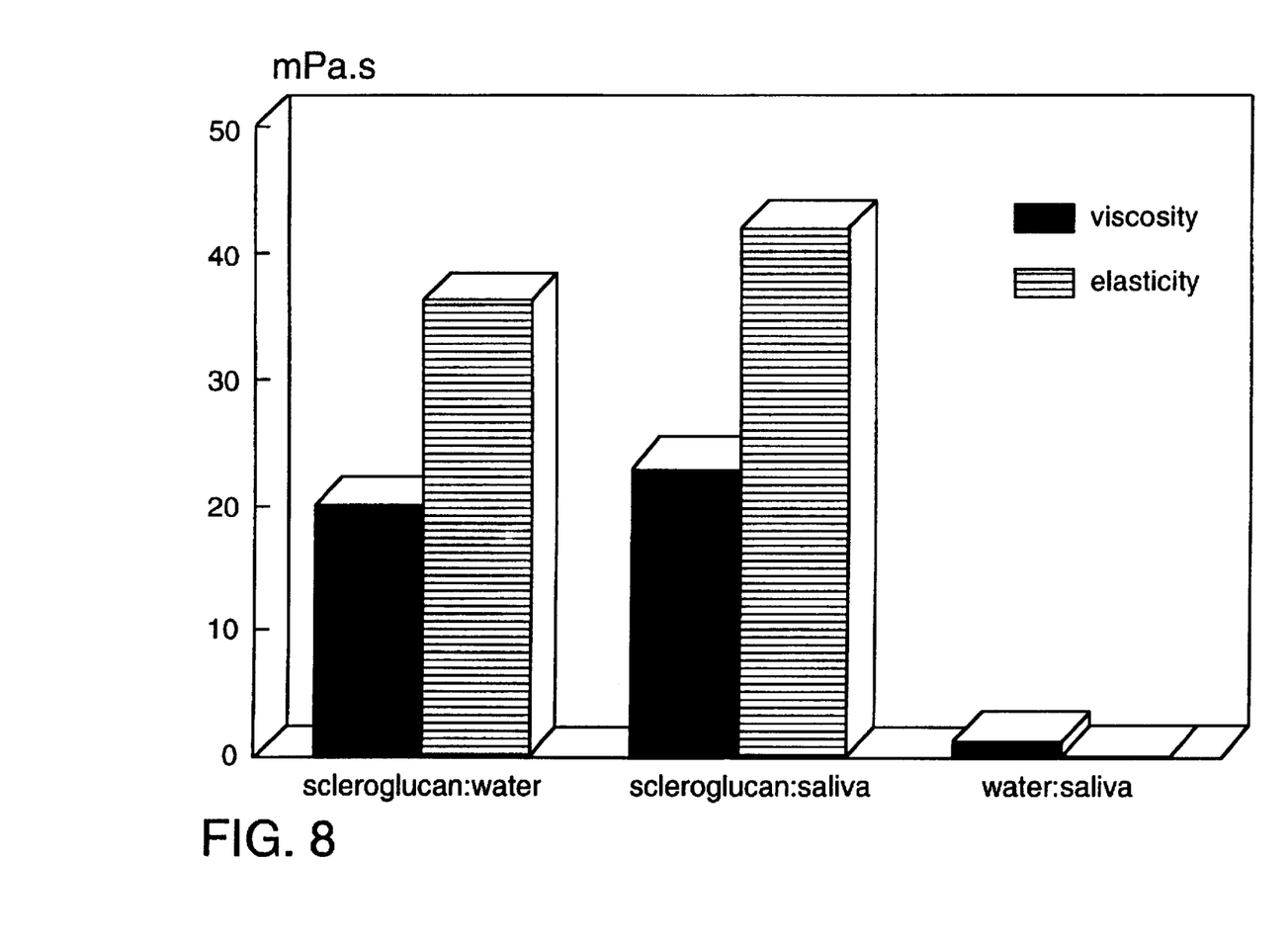
FIG. 8 illustrates that the increase in visco-elasticity of scleroglucan was only observed at a 10x-concentration but not at a viscosity level of saliva. ■ represents the viscosity; and ▨ the elasticity.

A number of polysaccharides exhibited fluctuations in visco-elasticity by varying the pH between 5 and 9, as shown in table 1. Xanthane gum and CMC displayed a slight increase in visco-elasticity in the pH range below pH 5 respectively 6. Alginic acid was very sensitive to pH changes (FIGS. 4 and 5). The visco-elasticity of polysaccharides can be sensitive to changes in ionic strength, mainly due to their hydration shell, which is dependent on the molecular weight, the form, the extent and type of substitution. Xanthane gum, alginic acid and CMC were relatively stable at more than 10 mM NaCl, while scleroglucan, guar gum and HEC were even rheologically stable between 0 and 0.2M NaCl (FIGS. 6 and 7) and further in the direction of 0.5M NaCl (not shown). Although all polysaccharides displayed an elastic response at a concentration of 0.1%, particularly the 'natural' polysaccharides scleroglucan and xanthane gum were elastic at relatively low (saliva) viscosity at a physiological pH (5–9) and at a physiological ionic strength (15–80 mM) (table 2 and FIG. 3).

Because calcium and fluoride ions are preferably added to a saliva substitute to remineralize the human enamel, the influence of these ions on the rheology was likewise investigated. Apart from alginic acid none of the polysaccharides displayed a specific ion-related behaviour. The polysaccharides alginic acid, xanthane gum and CMC, which were ionic strength sensitive for NaCl, were also sensitive to Ca$^{2+}$ and F$^-$. Precipitate formation of polysaccharide molecules on calcium ions was only observed in alginic acid, which even became completely insoluble through addition of trace amounts of CaCl$_2$ (Smidsrφc, et al., Acta Chem Scand. 26:2563–2566 (1972)). It was notable that no complex forming occurred of alginic acid with CCHS, although human saliva is a supersaturated calcium solution.

TABLE 1

A number of parameters which could have influenced the tested polysaccharides. − respectively + represent a decrease respectively increase in visco-elasticity, ● represents no change in visco-elasticity.

| Polysaccharide | pH | ionic strength (0–0.5 M NaCl) | Ca$^{2+}$ (0–0.5 M CaCl$_2$) | F (0.06 mM) | Influence on saliva |
|---|---|---|---|---|---|
| Alginic acid | ≦5 | — | flocculation | — | |
| Carboxymethyl cellulose | ≦6 | — | ● | — | ● |
| Hydroxyethyl cellulose | ● | ● | ● | ● | ● |
| Guar gum (Satia) | ● | ● | ● | ● | ● |
| Guar gum (Polysciences Inc.) | ● | ● | ● | ● | ● |
| Scleroglucan | ● | ● | ● | ● | +*/● |
| Xanthanegum | ≦5 | — | ● | ● | ● |

*Only observed for a scleroglucan concentration of at least 0.1%.

TABLE 2

Survey of the rheological properties of tested polysaccharides at a concentration of 0.1% and at a polymer-specific saliva simulating concentration Ẏ = 1.5 s$^{-1}$, T = 23.0° C. ± 1.5° C., ionic strength = 10 mM NaCl.

| Polysaccharides | Conc. % | η' | η" | Conc. (%) | η' | η" |
|---|---|---|---|---|---|---|
| Alginic acid | 0.1 | 3.4 | 0.13 | 0.05 | 1.8 | 0.05 |
| Carboxymethyl cellulose | 0.1 | 5.1 | 0.38 | 0.03 | 1.7 | 0.10 |
| Hydroxyethyl cellulose | 0.1 | 3.0 | 0.09 | 0.06 | 1.8 | 0.05 |
| Guar gum (Satia) | 0.1 | 1.5 | 0.04 | 0.1 | 1.5 | 0.04 |
| Guar gum (Polysciences Inc.) | 0.1 | 2.1 | 0.07 | 0.09 | 2.0 | 0.07 |
| Scleroglucan | 0.1 | 20.6 | 38.6 | 0.01 | 1.3 | 0.31 |
| Xanthane gum | 0.1 | 22.8 | 23.9 | 0.01 | 1.6 | 028 |
| Clarified complete human saliva | | | | | 2.1 | 0.77 |

5. Discussion

Earlier research has demonstrated that the rheological properties of saliva from the different glands varies markedly. In particular the sublingual saliva was found to be very elastic (Van der Reijden et al., 1993). It is therefore not possible to create a saliva substitute which reflects all Theological properties of the salivas from the different glands. Although complete saliva is a mixture of secretions the design of a saliva substitute has to be a homogenous system.

The criterion for a Theologically adequate saliva imitation can preferably be set at a viscosity η' between 1.5 and 3 mPa·s and an elasticity between 0.1 and 1 mPa·s at Y 1.5 s$^{-1}$. This range reflects the visco-elasticity of complete human saliva and saliva from the different glands (see FIG. 1) (Van der Reijden et al., 1993).

EXAMPLE 2

1. Materials and methods

Polyacrylic acid (PAA) which is available in the pharmaceutical qualities as Carbopol 974P® and Carbopol 934P®, has the particular property that it has a synergistic effect in respect of inter alia the high-molecular saliva mucin MG1. This has been determined in a subsequent experiment. Isolated human high-molecular saliva mucin from total saliva was incubated with PAA in a viscosity comparable to that of saliva. After overnight incubation the visco-elasticity was measured.

2. Results and discussion

Figure 9:
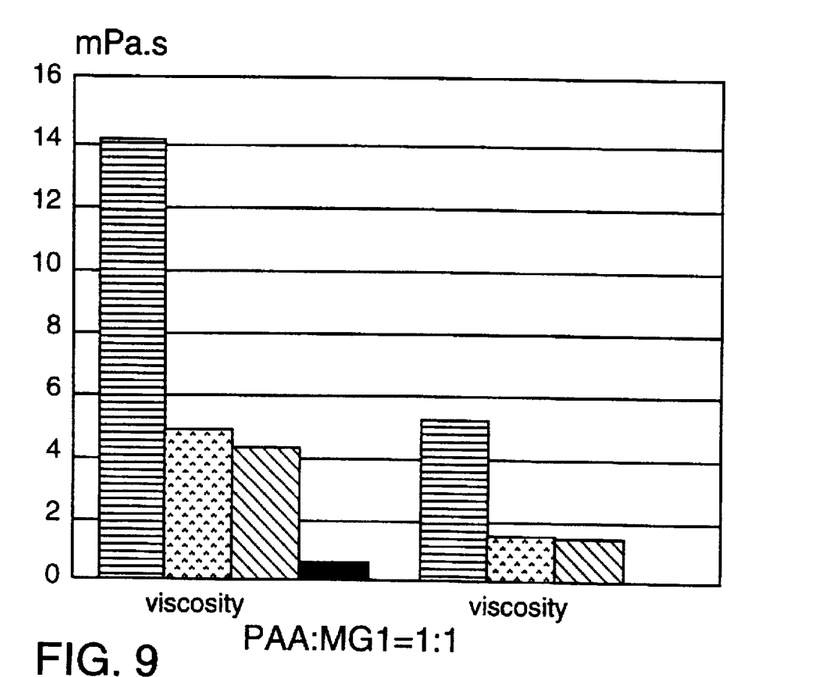
FIG. 9 shows the rheological synergism of polyacrylic acid with MG1-specific viscosity and elasticity. The left-hand side of the graph shows the viscosity, the right-hand side the elasticity. ≡ represents the combination of PAA+MG1; ▨ the calculated combination of PAA+MG1; ▨ the combination of water+MG1; ■ the combination of PAA+water.

It was found herefrom that the viscosity of a mixture of PAA and MG1 resulted in a higher viscosity than might be anticipated on the grounds of their individual viscosities (FIG. 9). Mixtures of PAA with water and MG1 with water served as controls. At a ratio of 1:1 this gave an increase in the viscosity of ±300% and an increase in the elasticity of ±250%, see FIG. 9. This can mean the following in vitro. Xerostomia patients who can produce a residual volume of saliva sometimes also have a quantity of mucin in their saliva. Because it is known that saliva mucins can adhere to both the surface of the teeth and to the oral mucosa, PAA could form a protective layer by adhering to this saliva mucin. This provides the additional possibility of lengthening the time of retention in the mouth so that the application frequency can be lowered.

From the experiments it was found that particularly xanthane gum, Guar gum, carboxymethyl cellulose, alginic acid and polyacrylic acid were exceptionally suitable polymers for application in a therapeutic composition according to the invention. Dissolved in HPLC-water they gave a clear visco-elastic solution. It was found from the experiments that scleroglucan in particular is completely ionic strength-insensitive, pH-insensitive and Theologically suitable, and therefore very useful for new artificial salivas. When xanthane gum is dissolved in a pH buffer at a low ionic strength (>10 mM NaCl), this polymer is likewise suitable.

The invention provides new compositions which can be used for various applications, such as in saliva substitutes or additives, tear water substitutes or additives, mouth rinses, toothpastes etc.

BRIEF DESCRIPTION OF THE DRAWINGS

Finally.

We claim:

1. A method of using an aqueous polymer compocition to enhance the saliva of a patient, comprising administering to a patient one or more effective doses of a composition consisting essentially of at least one polymer selected from the group consisting of scleroglucan and xanthane gum, wherein said polymer is present in the amount of about 0.01% in combination with at least one preservative and at least one electrolyte.

2. A method of using an aqueous polymer composition to enhance the saliva of a patient, comprising administering to a patient one or more effective doses of a composition consisting essentially of a 1:1 admixture or polyacrylic acid and mucin, in combination with at least one preservative and at least one electrolyte.

* * * * *

UNITED STATES PATENT AND TRADEMARK OFFICE
CERTIFICATE OF CORRECTION

PATENT NO. : 5,886,054
DATED : March 23, 1999
INVENTOR(S) : Arie Van Nieuw Amerongen et al.

It is certified that error appears in the above-identified patent and that said Letters Patent is hereby corrected as shown below:

Column 2 Line 41 between "for" and "their" delete period --.--.

Column 2 Lines 45-46, "(1993)
).﻿" should read --(1993)).--.

Column 2 Line 61 "Theological" should read --rheological--.

Column 4 Table 2, last column in row named "Xanthane gum": "028" should read --0.28--.

Column 4 Line 56 "Theological" should read --rheological--.

Column 4 Line 60 "Theologically" should read --rheologically--.

Column 4 Line 62 "Y" should read --Ẏ--.

Column 5 Line 16 "in-the" should read --in the-- (delete hyphen).

Column 5 Line 33 "Theologically" should read --rheologically--.

Column 5 Lines 44-45 "ron-stimulated" should read --non-stimulated--.

Column 5 Line 45 "o:" should read --of--.

UNITED STATES PATENT AND TRADEMARK OFFICE
CERTIFICATE OF CORRECTION

PATENT NO. : 5,886,054
DATED : March 23, 1999
INVENTOR(S) : Arie Van Nieuw Amerongen et al.

It is certified that error appears in the above-identified patent and that said Letters Patent is hereby corrected as shown below:

Column 6 Line 55 Claim 2 "admixture or" should read --admixture of--.

Signed and Sealed this

Sixteenth Day of November, 1999

*Attest:*

Q. TODD DICKINSON

*Attesting Officer*   *Acting Commissioner of Patents and Trademarks*